United States Patent
Scheibel et al.

(10) Patent No.: US 12,311,126 B2
(45) Date of Patent: May 27, 2025

(54) SECUREMENT DEVICE, KIT COMPRISING SECUREMENT DEVICE, AND METHOD OF SECURING SECUREMENT DEVICE ON SKIN OF USER

(71) Applicant: Solventum Intellectual Properties Company, Maplewood, MN (US)

(72) Inventors: Krystal J. Scheibel, Minneapolis, MN (US); James M. Sieracki, Plymouth, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/838,019

(22) PCT Filed: Feb. 16, 2023

(86) PCT No.: PCT/IB2023/051418
§ 371 (c)(1),
(2) Date: Aug. 13, 2024

(87) PCT Pub. No.: WO2023/161772
PCT Pub. Date: Aug. 31, 2023

(65) Prior Publication Data
US 2025/0114569 A1    Apr. 10, 2025

Related U.S. Application Data

(60) Provisional application No. 63/312,425, filed on Feb. 22, 2022.

(51) Int. Cl.
*A61M 25/02*    (2006.01)

(52) U.S. Cl.
CPC ....... *A61M 25/02* (2013.01); *A61M 2025/024* (2013.01); *A61M 2025/0266* (2013.01); *A61M 2205/0216* (2013.01)

(58) Field of Classification Search
CPC ............ A61M 25/02; A61M 2025/024; A61M 2025/0266; A61M 2205/0216
See application file for complete search history.

(56) References Cited

U.S. PATENT DOCUMENTS

| 6,134,477 A * | 10/2000 | Knuteson | A61N 1/0539 607/115 |
| 2003/0229313 A1 * | 12/2003 | Bierman | A61M 25/02 604/174 |
| 2005/0038453 A1 * | 2/2005 | Raulerson | A61M 25/02 606/151 |

FOREIGN PATENT DOCUMENTS

| EP | 1 048 320 A2 | 11/2000 |
| WO | WO 1999/025399 A1 | 5/1999 |

OTHER PUBLICATIONS

International Patent Application No. PCT/IB2023/051418, filed Feb. 16, 2023; International Search Report / Written Opinion issued Jun. 7, 2023; 12 pages.

* cited by examiner

*Primary Examiner* — Tasnim Mehjabin Ahmed

(57) ABSTRACT

A securement device (100) for securing a lumen (12) of a medical device (14) includes a main body (110) configured to be detachably secured to a skin of a user. The main body includes a first body portion (112) including a first cavity surface (118) and a second body portion (142) including a second cavity surface (148) pivotally coupled to the first cavity surface. The first and second cavity surfaces together define a cavity (170). The securement device further includes an insert (180) fixedly coupled to the main body and at least partially received within the cavity. The insert includes a groove (184) configured to receive the lumen of the medical device. The main body is deformable between an open configuration and a closed configuration, and the insert is correspondingly deformable between a release state (Continued)

and a secure state. In the release state, the groove is configured to receive the lumen therein. In the secure state, the lumen is secured within the groove.

29 Claims, 12 Drawing Sheets

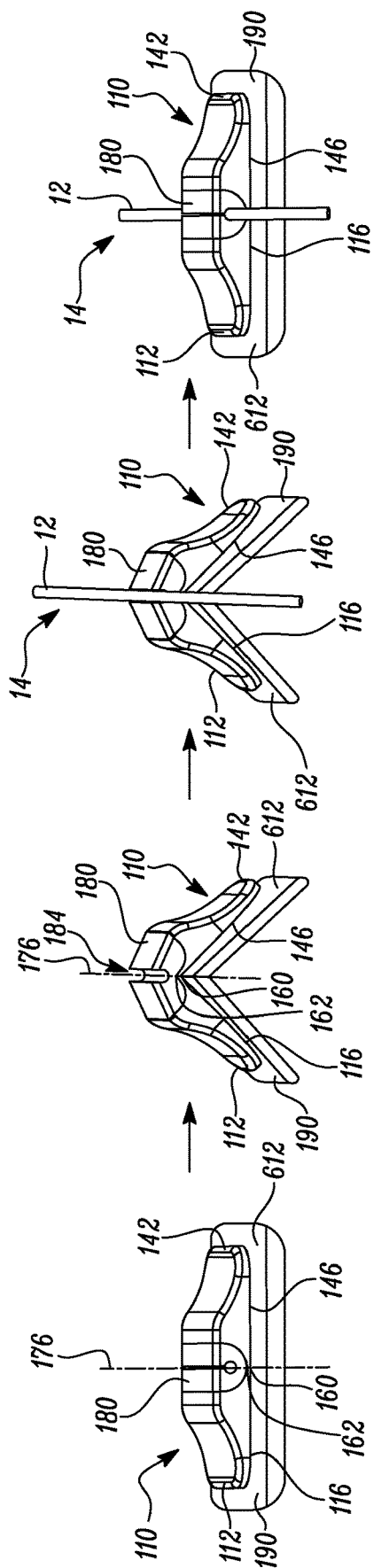

SECUREMENT DEVICE, KIT COMPRISING SECUREMENT DEVICE, AND METHOD OF SECURING SECUREMENT DEVICE ON SKIN OF USER

TECHNICAL FIELD

The present disclosure relates to a securement device for securing a lumen of a medical device on a skin of a user and a kit including the securement device. The present disclosure further relates to a method for securing the securement device on the skin of the user.

BACKGROUND

Various medical devices, such as, catheters, may be used for purposes, such as, feeding, air supply, and/or liquid removal. In some cases, such medical devices may be used to administer medications and fluids to a patient. In many instances, the medical devices may need to be secured on a skin of the patient to prevent movement of the medical devices. For example, the medical devices may need to be secured on the skin of the patient to prevent the medical devices from being pulled out, or otherwise move in ways that may adversely affect the functioning of the medical devices.

Generally, the medical devices may be secured on the skin of the patient using conventional securement means, such as, tapes, patches, and sutures. However, such conventional securement means may not properly secure the medical devices to the skin. In some cases, use of conventional securement means may result in various complications, such as, dislodgment and accidental removal of the medical devices from the skin of the patient, phlebitis, extravasation/infiltration, leakage, occlusion, and bloodstream infections. Additionally, conventional methods to secure the medical devices may create discomfort for the patients due to high fluid pressure in the medical devices.

In some examples, securement means, such as, tapes or patches, may allow partial or micro movement of the medical devices which can lead to discomfort for the patients. Further, conventional securement means may not provide proper coverage of an injection site, which may result in infection at the injection site. Moreover, use of sutures to secure the medical devices to the skin may lead to suture related infections and complications Thus, an improved securement means may be required to overcome the abovementioned challenges presented by conventional securement means.

SUMMARY

In a first aspect, the present disclosure provides a securement device for securing at least one lumen of a medical device. The securement device includes a main body having a first modulus of elasticity and configured to be detachably secured to a skin of a user. The main body includes a first body portion including a first upper surface, a first lower surface opposing the first upper surface, and a first cavity surface extending from the first upper surface partially towards the first lower surface. The main body further includes a second body portion pivotally coupled to the first body portion. The second body portion includes a second upper surface spaced apart from the first upper surface, a second lower surface pivotally coupled to the first lower surface along a first pivot interface, and a second cavity surface extending from the second upper surface partially towards the second lower surface. The second cavity surface is pivotally coupled to the first cavity surface along a second pivot interface spaced apart from the first pivot interface. The first cavity surface and the second cavity surface together define a cavity of the main body disposed between the first upper surface and the second upper surface. The securement device further includes an insert fixedly coupled to the main body and at least partially received within the cavity of the main body. The insert engages at least the first cavity surface of the first body portion, the second cavity surface of the second body portion, and the second pivot interface. The insert includes a groove along its length. The insert has a second modulus of elasticity less than the first modulus of elasticity. The insert is configured to at least partially and removably receive the at least one lumen within the groove. The main body is deformable between an open configuration and a closed configuration. The insert is deformable between a release state and a secure state based on a deformation of the main body between the open configuration and the closed configuration. The release state of the insert corresponds to the open configuration of the main body and the secure state of the insert corresponds to the closed configuration of the main body. In the open configuration of the main body, the first lower surface of the first body portion and the second lower surface of the second body portion are inclined to each other at the first pivot interface. Further, in the open configuration of the main body, the insert is in the release state, such that the groove is configured to removably and at least partially receive the at least one lumen therein. In the closed configuration of the main body, the first lower surface of the first body portion and the second lower surface of the second body portion are substantially parallel to each other at the first pivot interface. Further, in the closed configuration of the main body, the insert is in the secure state, such that the at least one lumen is secured within the groove.

In a second aspect, the present disclosure provides a kit. The kit includes a medical device including at least one lumen. The kit further includes a securement device for securing the at least one lumen of the medical device. The securement device includes a main body having a first modulus of elasticity and configured to be detachably secured to a skin of a user. The main body includes a first body portion including a first upper surface, a first lower surface opposing the first upper surface, and a first cavity surface extending from the first upper surface partially towards the first lower surface. The main body further includes a second body portion pivotally coupled to the first body portion. The second body portion includes a second upper surface spaced apart from the first upper surface, a second lower surface pivotally coupled to the first lower surface along a first pivot interface, and a second cavity surface extending from the second upper surface partially towards the second lower surface. The second cavity surface is pivotally coupled to the first cavity surface along a second pivot interface spaced apart from the first pivot interface. The first cavity surface and the second cavity surface together define a cavity of the main body disposed between the first upper surface and the second upper surface. The securement device further includes an insert fixedly coupled to the main body and at least partially received within the cavity of the main body. The insert engages at least the first cavity surface of the first body portion, the second cavity surface of the second body portion, and the second pivot interface. The insert includes a groove along its length. The insert has a second modulus of elasticity less than the first modulus of elasticity. The insert is configured to at least partially and removably receive the at least one lumen within the groove. The main body is deformable between an open configuration and a closed configuration. The insert is deformable between a release state and a secure state based on a deformation of the main body between the open configuration and the closed configuration. The release state of the insert corresponds to the open configuration of the main body and the secure state of the insert corresponds to the closed configuration of the main body. In the open configuration of the main body, the first lower surface of the first body portion and the second lower surface of the second body portion are inclined to each other at the first pivot interface. Further, in the open configuration of the main body, the insert is in the release state, such that the groove is configured to removably and at least partially receive the at least one lumen therein. In the closed configuration of the main body, the first lower surface of the first body portion and the second lower surface of the second body portion are substantially parallel to each other at the first pivot interface. Further, in the closed configuration of the main body, the insert is in the secure state, such that the at least one lumen is secured within the groove.

In a third aspect, the present disclosure provides a method of securing a securement device on a skin of a user. The securement device includes a main body including a first body portion and a second body portion. The securement device includes an insert fixedly coupled to the main body. The method includes deforming the main body to an open configuration. In the open configuration of the main body, a first lower surface of the first body portion and a second lower surface of the second body portion are inclined to each other at a first pivot interface. The method further includes deforming the insert to a release state based on a deformation of the main body to the open configuration. The release state of the insert corresponds to the open configuration of the main body. The method further includes engaging the at least one lumen with the insert upon a deformation of the insert to the release state. When the insert is in the release state, a groove of the insert is configured to removably and at least partially receive the at least one lumen therein. The method further includes deforming the main body to a closed configuration. In the closed configuration of the main body, the first lower surface of the first body portion and the second lower surface of the second body portion are substantially parallel to each other at the first pivot interface. The method further includes deforming the insert to a secure state based on the deformation of the main body to the closed configuration. The secure state of the insert corresponds to the closed configuration of the main body. The method further includes securing the at least one lumen within the groove upon the deformation of the insert to the secure state.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

Exemplary embodiments disclosed herein is more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labelled with the same number.

FIGS. 11A to 11F illustrate various steps for securing the securement device on the skin of the user, according to an embodiment of the present disclosure.

DETAILED DESCRIPTION

Figure 1:
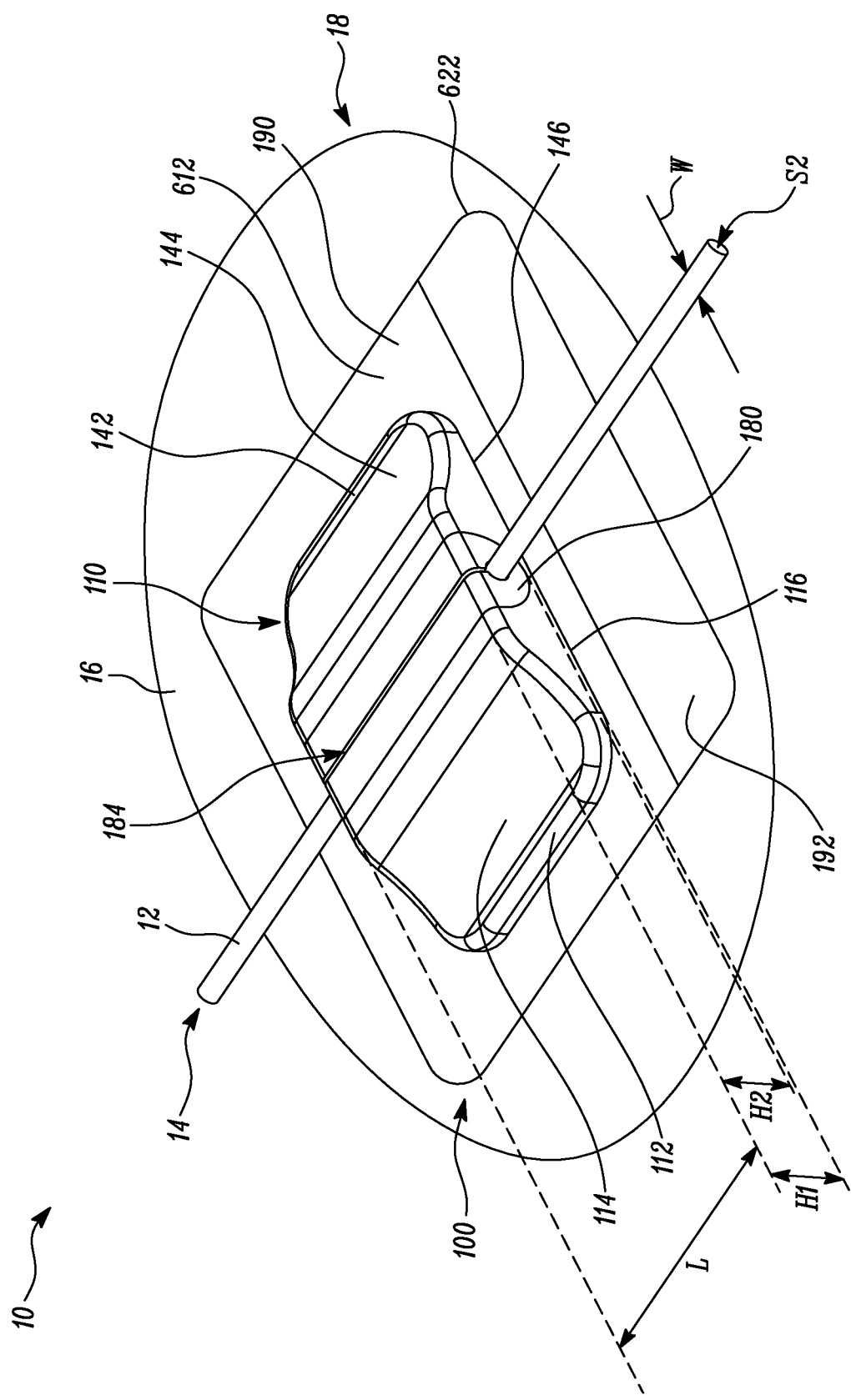
FIG. 1 is a schematic perspective view of a kit including a securement device, according to an embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

In the following disclosure, the following definitions are adopted.

As recited herein, all numbers should be considered modified by the term "about". As used herein, "a," "an," "the," "at least one," and "one or more" are used interchangeably.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties).

The term "substantially", unless otherwise specifically defined, means to a high degree of approximation (e.g., within +/−10% for quantifiable properties) but again without requiring absolute precision or a perfect match.

The term "about", unless otherwise specifically defined, means to a high degree of approximation (e.g., within +/−5% for quantifiable properties) but again without requiring absolute precision or a perfect match.

Terms, such as, same, equal, uniform, constant, strictly, and the like, are understood to be within the usual tolerances or measuring error applicable to the particular circumstance rather than requiring absolute precision or a perfect match.

As used herein, the terms "first" and "second" are used as identifiers. Therefore, such terms should not be construed as limiting of this disclosure. The terms "first" and "second" when used in conjunction with a feature or an element can be interchanged throughout the embodiments of this disclosure.

As used herein, when a first material is termed as "similar" to a second material, at least 90 weight % of the first and second materials are identical and any variation between the first and second materials comprises less than about 10 weight % of each of the first and second materials.

As used herein, "at least one of A and B" should be understood to mean "only A, only B, or both A and B".

Unless specified or limited otherwise, the terms "attached," "connected," and variations thereof, are used broadly and encompass both direct and indirect attachments, connections, and couplings.

As used herein, the terms "layer," "sheet," and "dressing," or variations thereof, are used to describe an article having a thickness that is small relative to its length and width.

As used herein, the term "polymer" refers to both materials prepared from one monomer, such as, a homopolymer or to materials prepared from two or more monomers, such as, a copolymer, terpolymer, or the like. Likewise, the term "polymerize" refers to the process of making a polymeric material that can be a homopolymer, copolymer, terpolymer, or the like. The term "copolymer" refers to a polymeric material prepared from at least two different monomers.

As used herein, the term "modulus of elasticity" (also interchangeably referred to as Young's modulus or storage modulus) refers to a quantity that measures a material's resistance to being deformed elastically when a stress is applied to it. Essentially, the modulus of elasticity is a quantitative measure of the stiffness of an elastic material that measures the ability of the material under test to recover to its original shape or size. Modulus of elasticity can be calculated using an equation derived by Hooke's law, where the modulus of elasticity is equal to a ratio of stress to strain (i.e., ratio of applied force to change in fraction of size).

The present disclosure relates to a securement device for securing at least one lumen of a medical device, a kit including the securement device, and a method of securing the securement device on a skin of a user. The securement device includes a main body having a first modulus of elasticity and configured to be detachably secured to the skin of the user. The main body includes a first body portion including a first upper surface, a first lower surface opposing the first upper surface, and a first cavity surface extending from the first upper surface partially towards the first lower surface. The main body further includes a second body portion pivotally coupled to the first body portion. The second body portion includes a second upper surface spaced apart from the first upper surface, a second lower surface pivotally coupled to the first lower surface along a first pivot interface, and a second cavity surface extending from the second upper surface partially towards the second lower surface. The second cavity surface is pivotally coupled to the first cavity surface along a second pivot interface spaced apart from the first pivot interface. The first cavity surface and the second cavity surface together define a cavity of the main body disposed between the first upper surface and the second upper surface. The securement device further includes an insert fixedly coupled to the main body and at least partially received within the cavity of the main body. The insert engages at least the first cavity surface of the first body portion, the second cavity surface of the second body portion, and the first pivot interface. The insert includes a groove along its length. The insert has a second modulus of elasticity less than the first modulus of elasticity. The insert is configured to at least partially and removably receive the at least one lumen within the groove. The main body is deformable between an open configuration and a closed configuration. The insert is deformable between a release state and a secure state based on a deformation of the main body between the open configuration and the closed configuration. The release state of the insert corresponds to the open configuration of the main body and the secure state of the insert corresponds to the closed configuration of the main body. In the open configuration of the main body, the first lower surface of the first body portion and the second lower surface of the second body portion are inclined to each other at the first pivot interface. Further, in the open configuration of the main body, the insert is in the release state, such that the groove is configured to removably and at least partially receive the at least one lumen therein. In the closed configuration of the main body, the first lower surface of the first body portion and the second lower surface of the second body portion are substantially parallel to each other at the first pivot interface. Further, in the closed configuration of the main body, the insert is in the secure state, such that the at least one lumen is secured within the groove.

Medical devices, such as, catheters, may be used for various purposes, such as, feeding, air supply, and/or liquid removal. In some cases, the medical devices may be used to administer medications and fluids to a user, such as, a patient in need of a medical therapy. In many instances, the medical device may need to be secured on the skin of the user to prevent movement of the medical devices. For example, the medical devices may need to be secured on the skin of the user to prevent the medical devices from being pulled out, or otherwise move in ways that may adversely affect the functioning of the medical devices.

Conventionally, the medical devices may be secured on the skin of the user using securement means, such as, tapes, patches, and/or sutures. However, such conventional securement means may not properly secure the medical devices to the skin. For example, securement means, such as, sutures may require great skill, and if the sutures are not properly administered, the medical devices may not only be improperly secured on the skin, but the user may also feel discomfort at a site of the sutures. Other securement means, such as, tapes and patches, may allow partial or micro movement of the medical devices, which may lead to discomfort for the users. Further, the tapes and patches may use adhesives that may not be easily removable, thus requiring additional adhesive removers or alcohol for removal. Furthermore, conventional securement means may not provide proper coverage of an injection site, which may result in an infection at the injection site.

The securement device of the present disclosure may secure the at least one lumen of the medical device firmly to the skin of the user. The securement device may further allow lumens of different sizes and/or shapes to be secured within the groove of the insert. Further, a base of the securement device may be removably secured to the skin of the user. The base may include one or more pull tabs that may be gripped by a clinician and pulled to detach the base from the skin of the user. An adhesive layer may firmly secure the base on the skin of the user. The adhesive layer may include a stretch release adhesive, such that, based on a stretching of the base, the adhesive layer may lose its adhesion property. Subsequently, the base may be easily released to remove the securement device from the skin of the user. In other words, the base may be easily removed from the skin of the user without causing discomfort to the user. Further, the securement device may prevent dislodgement and accidental removal of the medical device from the skin of the user.

Thus, the securement device of the present disclosure may firmly secure the medical device to the skin of the user, may inhibit undesirable movement of the medical device, may prevent infection at the injection site, and may facilitate easy removal of the securement device after use.

Referring now to figures, FIG. 1 illustrates a schematic perspective view of a kit 10, according to an embodiment of the present disclosure. The kit 10 includes a medical device 14 including at least one lumen 12. In some embodiments, the at least one lumen 12 may be a catheter used for purposes, such as, to administer an intravenous therapy (e.g., medication or fluids for parenteral nutrition), to obtain blood for analysis, and/or to provide an access point for blood-based treatments, such as, dialysis or apheresis. The catheter may be used to measure one or more properties of the blood (e.g., a "central venous oxygen saturation"), administer fluid or blood products for a large volume resuscitation, and/or measure a central venous pressure. In some cases, the catheter may be a central venous catheter (CVC). The CVC, also referred to as a central line, a central venous line, or a central venous access catheter, may be used to access large, centrally located veins of the user, which may be required for critically ill patients, for patients requiring prolonged intravenous therapies for reliable vascular access, and to administer fluids that may harm smaller peripheral veins. The PVC may be inserted into veins located at a neck (e.g., an internal jugular vein), into veins located at a chest (e.g., a subclavian vein or axillary vein), or into veins located at a groin (e.g., a femoral vein) of the user. In some cases, the catheter may be a peripherally inserted central catheter (PICC). The PICC may be suitable for insertion into veins located at an arm of the user. In some other cases, the catheter may be any other suitable type of catheter, which may be selected based on desired application attributes.

In some embodiments, the at least one lumen 12 may be made from a medical grade material, such as, any one or combinations of polyvinylchloride (PVC), silicone, silicone-coated latex, polyurethane (PU), low-density polyethylene (LDPE), metallocene polyolefins, silicones, polyamide (PA), polyesters, and the like. Silicone may include silicones cured by moisture or hydrosilation. Metallocene polyolefins may include metallocene polyethylene and metallocene polypropylene. Polyesters may include elastomeric polyesters, such as, Hytrel brand polyesters, fluoropolymers, such as, Teflon and fluor elastomers, and the like. The lumen 12 may also include blends, mixtures, laminates, and/or coextrusions of one or more of the above-mentioned materials.

In some embodiments, the lumen 12 may have a minimum width W. The minimum width W may be defined as a distance between outermost walls of the lumen 12. In the illustrated embodiment of FIG. 1, the lumen 12 may have a circular cross-section. In such cases, the minimum width W may be defined as a diameter of the lumen 12. In some other cases, the lumen 12 may include any other cross-section. In such cases, the minimum width W may be defined as a diameter of a circumscribed circle about a geometry of the cross-section. Further, the minimum width W of the lumen 12 may be from about 1 millimeter (mm) to about 8 mm, without any limitations.

The kit 10 also includes a securement device 100 for securing the at least one lumen 12 of the medical device 14. In some embodiments, the securement device 100 may be detachably secured to a skin 16 of a user 18, for example a patient. In the illustrated embodiment of FIG. 1, the kit 10 includes the single lumen 12 that may be coupled to the securement device 100. Alternatively, the kit 10 may include more than one lumen 12, without any limitations. In some embodiments, the kit 10 may further include gloves (not shown). In some embodiments, the kit 10 may further include a sterilizing material (not shown). In some embodiments, the kit 10 may further include a cloth or other absorbent material (not shown). In some embodiments, the kit 10 may further include cleaning articles (not shown), such as, cleaning cloths, cotton balls, cotton swabs, and the like. The kit 10 may be available to clinicians (or medical professionals) for use in a sterilized package.

Further, the securement device 100 includes a main body 110. The main body 110 is configured to be detachably secured to the skin 16 of the user 18. In some embodiments, the main body 110 may be a single-piece integral component. However, in some other embodiments, the main body 110 may include a plurality of discrete pieces that may be assembled to form the main body 110. The main body 110 has a first modulus of elasticity E1. In some embodiments, the first modulus of elasticity E1 may be from about 1 gigapascal (GPa) to about 5 GPa. In some embodiments, the main body 110 may include at least one of a polymer, an elastomer, and a metal. In some embodiments, the main body 110 may include a combination of different materials. In some embodiments, the main body 110 may include any one of plastics and composites. In some embodiments, the main body 110 may include one or more of acrylonitrile butadiene styrene (ABS), polypropylene, polycarbonate, polyethylene, PVC, nylon, olefins, acrylics, polyesters, silicones, thermoplastic urethane, thermoplastic elastomers, and the like, without any limitations.

Figure 2A:
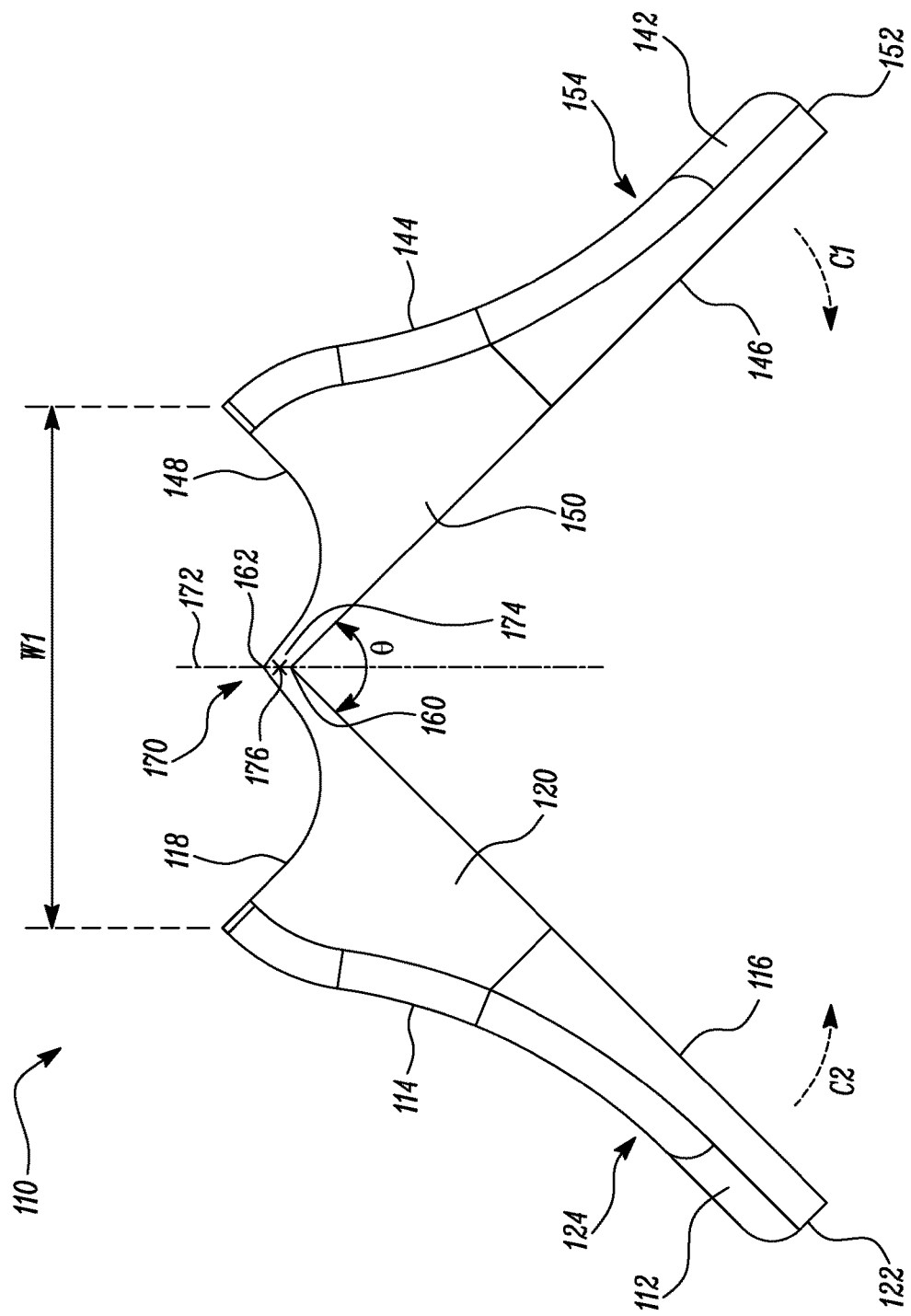
FIG. 2A is a schematic side view of a main body of the securement device, according to an embodiment of the present disclosure.
Figure 2B:
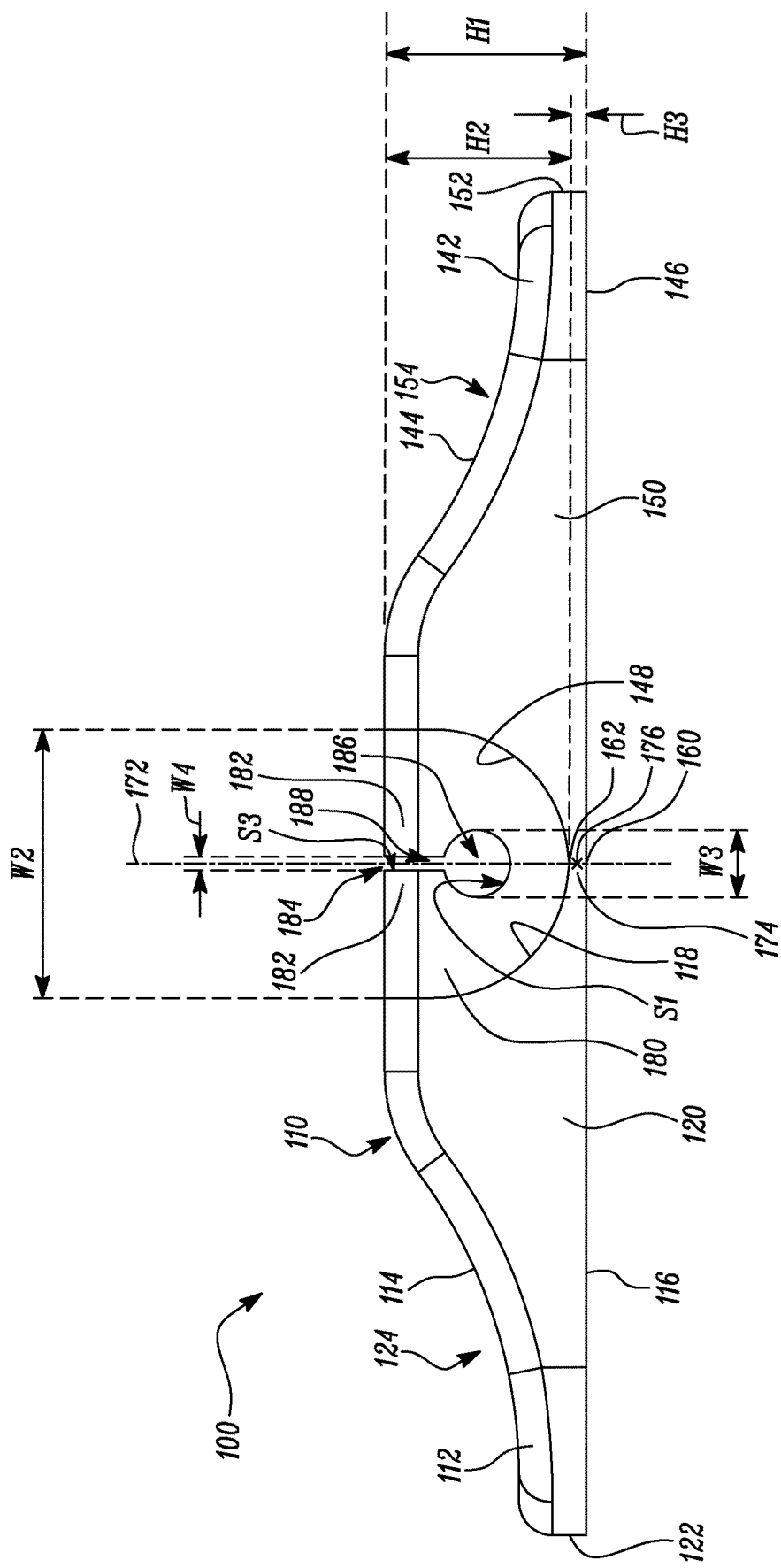
FIG. 2B is a schematic side view of the securement device with a base not shown, according to an embodiment of the present disclosure.
Figure 3:
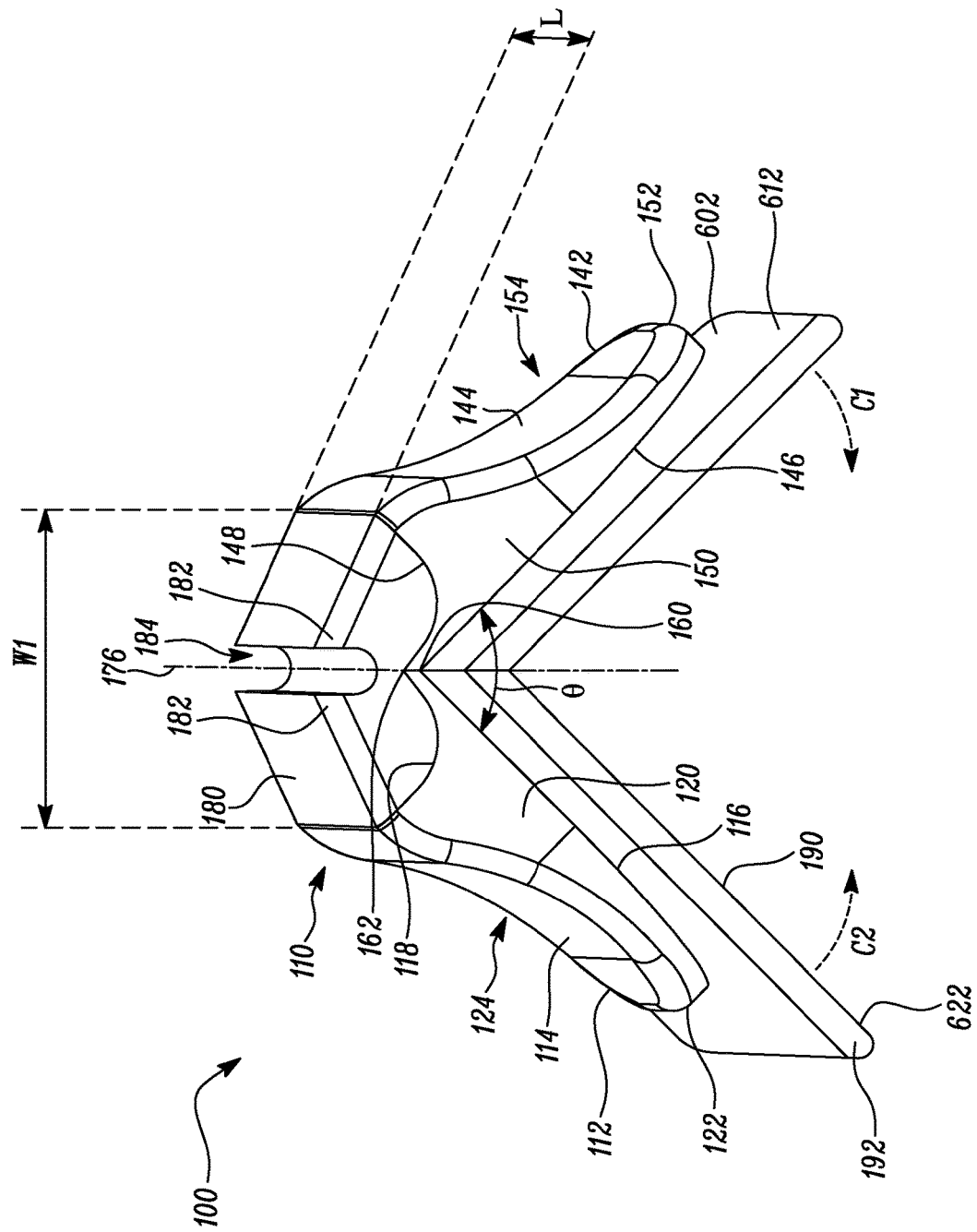
FIG. 3 is a schematic perspective view of the securement device illustrating the main body in an open configuration, according to an embodiment of the present disclosure.

FIG. 2A illustrates a schematic side view of the main body 110 of the securement device 100, according to an embodiment of the present disclosure. Referring to FIG. 2A, the main body 110 includes a first body portion 112 including a first upper surface 114, a first lower surface 116 opposing the first upper surface 114, and a first cavity surface 118 extending from the first upper surface 114 partially towards the first lower surface 116. The main body 110 is deformable between an open configuration (as illustrated in FIGS. 2A and 3) and a closed configuration (as illustrated in FIGS. 1 and 2B).

In some embodiments, the first body portion 112 may further include a pair of first lateral surfaces 120 (only one of which is shown in FIG. 2A) opposing each other and extending between the first upper surface 114 and the first lower surface 116. In some embodiments, the first body portion 112 may further include a first end surface 122 disposed distal to the first cavity surface 118 and extending between the pair of first lateral surfaces 120. In some embodiments, the first end surface 122 may be further disposed between the first upper surface 114 and the first lower surface 116. Further, in some embodiments, the first cavity surface 118 may extend between the pair of first lateral surfaces 120.

In some embodiments, the first body portion 112 may taper at least partially from a cavity 170 towards the first end surface 122, such that the first body portion 112 may further include a first gripping region 124 disposed adjacent to the first end surface 122. In the illustrated embodiment of FIG. 2A, the first upper surface 114 may be substantially curved. In some other embodiments, the first upper surface 114 may be substantially planar. Further, the first gripping region 124 may include one or more textures that may improve gripping characteristics of the securement device 100. For example, the first gripping region 124 may include a knurled surface.

The main body 110 further includes a second body portion 142 pivotally coupled to the first body portion 112. The second body portion 142 includes a second upper surface 144 spaced apart from the first upper surface 114, a second lower surface 146 pivotally coupled to the first lower surface 116 along a first pivot interface 160, and a second cavity surface 148 extending from the second upper surface 144 partially towards the second lower surface 146. In some embodiments wherein the main body 110 is embodied as the single-piece integral component, the first lower surface 116 of the first body portion 112 and the second lower surface 146 of the second body portion 142 may be a part of a same monolith of the main body 110. Thus, the first lower surface 116 and the second lower surface 146 may be pivotable due to a deformation of the main body 110 along the first pivot interface 160. In some embodiments, the securement device 100 may be secured on the skin 16 (see FIG. 1) of the user 18 (see FIG. 1), such that the first lower surface 116 of the first body portion 112 and the second lower surface 146 of the second body portion 142 may be proximal to the skin 16 of the user 18, and the first upper surface 114 of the first body portion 112 and the second upper surface 144 of the second body portion 142 may be distal to the skin 16 of the user 18.

Further, the second cavity surface 148 is pivotally coupled to the first cavity surface 118 along a second pivot interface 162 spaced apart from the first pivot interface 160. The first cavity surface 118 and the second cavity surface 148 together define the cavity 170 of the main body 110 disposed between the first upper surface 114 and the second upper surface 144. When the main body 110 is in the closed configuration, the cavity 170 includes a generally semi-circular shape. Alternatively, the cavity 170 may include any other shape when the main body 110 is in the closed configuration, without any limitations.

In some embodiments wherein the main body 110 is embodied as the single-piece integral component, the first cavity surface 118 of the first body portion 112 and the second cavity surface 148 of the second body portion 142 may be a part of the same monolith of the main body 110. Thus, the first cavity surface 118 and the second cavity surface 148 may be pivotable due to the deformation of the main body 110 along the second pivot interface 162. In some embodiments, the first pivot interface 160 and the second pivot interface 162 may be spaced apart from each other in the same monolith of the main body 110. Thus, the deformation of the main body 110 along the first pivotal interface 160 may result in a corresponding deformation of the main body 110 along the second pivotal interface 162. In other words, a pivotal movement of the first lower surface 116 relative to the second lower surface 146 may result in a corresponding pivotal movement of the first cavity surface 118 relative to the second cavity surface 148. Further, in some embodiments, the first pivot interface 160 and the second pivot interface 162 may be spaced apart from each other along a normal axis 172. Moreover, the main body 110 may define a portion 174 of the main body 110, which separates the first and second pivot interfaces 160, 162.

In some embodiments, the second body portion 142 may further include a pair of second lateral surfaces 150 (only one of which is shown in FIG. 2A) opposing each other and extending between the second upper surface 144 and the second lower surface 146. In some embodiments, the second body portion 142 may further include a second end surface 152 disposed distal to the second cavity surface 148. In some embodiments, the second end surface 152 may extend between the pair of second lateral surfaces 150. In some embodiments, the second end surface 152 may be further disposed between the second upper surface 144 and the second lower surface 146. Further, in some embodiments, the second cavity surface 148 may extend between the pair of second lateral surfaces 150.

In some embodiments, each of the pair of second lateral surfaces 150 may be joined to a corresponding first lateral surface 120 from the pair of first lateral surfaces 120 of the first body portion 112 between the first pivot interface 160 and the second pivot interface 162.

In some embodiments, the second body portion 142 may taper at least partially from the cavity 170 towards the second end surface 152, such that the second body portion 142 may further include a second gripping region 154 disposed adjacent to the second end surface 152. In the illustrated embodiment of FIG. 2A, the second upper surface 144 may be substantially curved. In some other embodiments, the second upper surface 144 may be substantially planar. Further, the second gripping region 154 may include one or more textures that may improve the gripping characteristics of the securement device 100. For example, the second gripping region 154 may include a knurled surface.

Referring to FIGS. 1 and 2A, the securement device 100 may further include a base 190. In some embodiments, the securement device 100 may be removably secured on the skin 16 of the user 18, such that the base 190 of the securement device 100 is in contact with the skin 16 of the user 18. The base 190 may include a pull tab 192 disposed along a perimeter 622 of the base 190, that may be used to remove the securement device 100 from the skin 16 of the user 18. Specifically, the pull tab 192 may assist clinicians during a detachment of the base 190 from the skin 16 of the user 18.

FIG. 2B illustrates a schematic side view of the securement device 100, according to an embodiment of the present disclosure. The base 190 is not shown in FIG. 2B for the purpose of clarity. Referring to FIG. 2B, the securement device 100 further includes an insert 180 fixedly coupled to the main body 110 and at least partially received within the cavity 170 (see FIG. 2A) of the main body 110. In some embodiments, the insert 180 may extend between the pair of first lateral surfaces 120 (only one of which is shown in FIG. 2B). In some embodiments, the insert 180 may extend between the pair of second lateral surfaces 150 (only one of which is shown in FIG. 2B).

Referring to FIGS. 1 and 2B, the insert 180 engages at least the first cavity surface 118 of the first body portion 112, the second cavity surface 148 of the second body portion 142, and the second pivot interface 162. The insert 180 includes a groove 184 along its length L. Further, the insert 180 has a second modulus of elasticity $E2$ less than the first modulus of elasticity $E1$. In some embodiments, the first modulus of elasticity $E1$ of the main body 110 may be greater than the second modulus of elasticity $E2$ of the insert 180 by a factor of at least 2. In some embodiments, the first modulus of elasticity $E1$ of the main body 110 may be greater than the second modulus of elasticity $E2$ of the insert 180 by a factor of at least 3, at least 4, at least 5, at least 6, at least 8, or at least 10. In some embodiments, the second modulus of elasticity E2 may be about 1 GPa. However, in some embodiments, the second modulus of elasticity E2 may be about 0, i.e., the insert 180 may be substantially plastic. In some embodiments, the insert 180 may include an elastomer. In some embodiments, the insert 180 may include silicones, polydimethylsiloxane (PDMS), liquid silicone rubber, poly(styrene-butadiene-styrene), other suitable thermoplastic elastomers, and/or combinations thereof.

Further, the insert 180 is configured to at least partially and removably receive the at least one lumen 12 (see FIG. 1) within the groove 184. In some embodiments, the groove 184 of the insert 180 may include a first groove portion 186 disposed proximal to the second pivot interface 162 and a second groove portion 188 extending from the first groove portion 186 away from the second pivot interface 162. In some embodiments, the insert 180 may include two split insert portions 182 defining the second groove portion 188 therebetween, such that the second groove portion 188 is open.

Further, the insert 180 is deformable between a release state (as illustrated in FIG. 3) and a secure state (as illustrated in FIGS. 1 and 2B) based on a deformation of the main body 110 between the open configuration and the closed configuration. The release state of the insert 180 corresponds to the open configuration of the main body 110 and the secure state of the insert 180 corresponds to the closed configuration of the main body 110. In some embodiments, the main body 110 and the insert 180 may be deformable about a common pivot axis 176 (also shown in FIG. 3). In some embodiments, the common pivot axis 176 may be substantially orthogonal to the normal axis 172. As can be observed in FIG. 3, the length L of the insert 180 may substantially extend along the common pivot axis 176. Therefore, directions of the deformation of the main body 110 and the deformation of the insert 180 about the common pivot axis 176 may be substantially similar.

FIG. 3 is a schematic perspective view of the securement device 100 illustrating the main body 110 in the open configuration, according to an embodiment of the present disclosure.

In the open configuration of the main body 110, the first lower surface 116 of the first body portion 112 and the second lower surface 146 of the second body portion 142 are inclined to each other at the first pivot interface 160. In some embodiments, the main body 110 may be deformed to the open configuration based on a movement of the first body portion 112 in an anti-clockwise direction C2 and a movement of the second body portion 142 in a clockwise direction C1. For example, clinicians may hold the first body portion 112 by their left hand to effectuate the movement of the first body portion 112 in the anti-clockwise direction C2. In some examples, clinicians may hold the first body portion 112 at the first gripping region 124 and the first lower surface 116. Further, clinicians may hold the second body portion 142 by their right hand to effectuate the movement of the second body portion 142 in the clockwise direction C1. In some examples, clinicians may hold the second body portion 142 at the second gripping region 154 and the second lower surface 146. The movement of the first and second body portions 112, 142 may deform the main body 110 along the first and second pivot interfaces 160, 162. Further, the first body portion 112 and the second body portion 142 may pivot about the common pivot axis 176, such that first lower surface 116 of the first body portion 112 and the second lower surface 146 of the second body portion 142 move towards each other and form an angle θ at the first pivot interface 160.

In some cases, the first and second body portions 112, 142 may be moved by the same angular distance. In some other cases, the first and second body portions 112, 142 may be moved by different angular distances. It may also be contemplated that clinicians may hold one of the first and second body portions 112, 142 stationary, and may only move the other of the first and second body portions 112, 142.

In some embodiments, the deformation of the main body 110 may also cause a deformation of the cavity 170. In some embodiments, the cavity 170 may have a first maximum cavity width W1 in the open configuration of the main body 110 and a second maximum cavity width W2 (shown in FIG. 2B) in the closed configuration of the main body 110. Further, the first maximum cavity width W1 may be greater than the second maximum cavity width W2. Moreover, the deformation of the main body 110 may also cause a deformation of the insert 180, such that the split insert portions 182 of the insert 180 may move apart from each other with respect to the common pivot axis 176. In the open configuration of the main body 110, the insert 180 is in the release state, such that the groove 184 is configured to removably and at least partially receive the at least one lumen 12 therein. Specifically, the first groove portion 186 may be configured to removably and at least partially receive the at least one lumen 12 therein.

Figure 4:
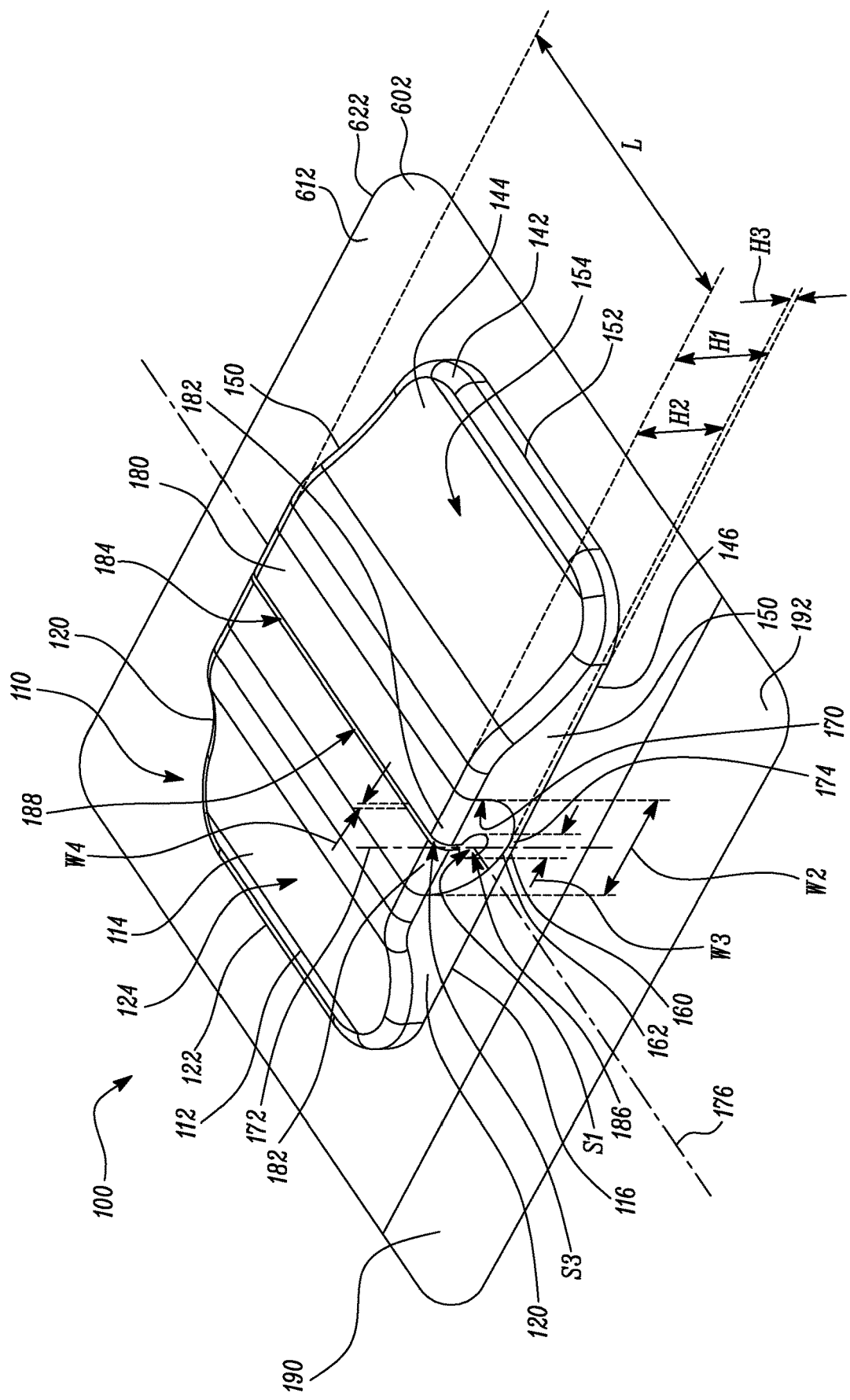
FIG. 4 is a schematic perspective view of the securement device illustrating the main body in the closed configuration, according to an embodiment of the present disclosure.

FIG. 4 illustrates the main body 110 in the closed configuration, according to an embodiment of the present disclosure. Referring to FIGS. 3 and 4, in the closed configuration of the main body 110, the first lower surface 116 of the first body portion 112 and the second lower surface 146 of the second body portion 142 are substantially parallel to each other at the first pivot interface 160. In some embodiments, the closed configuration of the main body 110 may be a normal state of the main body 110. When the main body 110 moves to the closed configuration from the open configuration, the first lower surface 116 of the first body portion 112 and the second lower surface 146 of the second body portion 142 move away from each other. In other words, the first body portion 112 may move in the clockwise direction C1 and the second body portion 142 may move in the anti-clockwise direction C2 with respect to the common pivot axis 176.

In some embodiments, the deformation of the main body 110 to the closed configuration may also cause the deformation of the cavity 170 (see FIG. 2A), such that the cavity 170 may have the second maximum cavity width W2 in the closed configuration of the main body 110. In some embodiments, the secure state of the insert 180 may be a normal state of the insert 180. Thus, when the main body 110 moves to the closed configuration, the insert 180 may also move to the secure state. In the closed configuration of the main body 110, the insert 180 is in the secure state, such that the at least one lumen 12 (see FIG. 1) is secured within the groove 184. In some embodiments, the at least one lumen 12 may be secured within the first groove portion 186.

Generally, in the secure state of the insert 180, the at least one lumen 12 may be secured within the securement device 100, such that any movement of the lumen 12 may be restricted without deforming the at least one lumen 12. Thus, in the secure state of the insert 180, the first groove portion 186 may include a cross-sectional shape S1 that is similar to a cross-sectional shape S2 (see FIG. 1) of the lumen 12. In some embodiments, when the main body 110 is in the closed configuration, the shape of the cavity 170 may be substantially similar to the cross-sectional shape S1 of the first groove portion 186, such that the first groove portion 186 may be concentric with the cavity 170 (also shown in FIG. 2A). In the illustrated embodiment of FIG. 4, the cavity 170 includes the semi-circular shape and the first groove portion 186 includes the cross-sectional shape S1. In other embodiments, the cavity 170 may have a rectangular shape or a square shape, and the first groove portion 186 may include the circular cross-sectional shape S1.

In some embodiments, in the secure state of the insert 180, the first groove portion 186 may include the cross-sectional shape S1 that conforms to the cross-sectional shape S2 of the at least one lumen 12. Further, in the secure state of the insert 180, the first groove portion 186 may include the circular cross-sectional shape S1 and the second groove portion 188 may include a rectangular cross-sectional shape S3 (shown in FIG. 4). Therefore, in the secure state of the insert 180, the groove 184 may be substantially keyhole-shaped. However, in some other embodiments, the first groove portion 186 and the second groove portion 188 may include other cross-sectional shapes, according to desired application attributes. For example, the first groove portion 186 may include a square cross-sectional shape or a rectangular cross-sectional shape.

Further, in the secure state of the insert 180, the first groove portion 186 defines a first maximum groove width W3 and the second groove portion 188 defines a second maximum groove width W4. In some embodiments, in the secure state, the first maximum groove width W3 of the first groove portion 186 may be greater than the second maximum groove width W4 of the second groove portion 188 by a factor of at least 2. In other embodiments, the first maximum groove width W3 of the first groove portion 186 may be greater than the second maximum groove width W4 of the second groove portion 188 by a factor of at least 2.5, 3, 4, 5, and the like, without any limitations. Further, in some embodiments, in the secure state of the insert 180, the second maximum groove width W4 of the second groove portion 188 may be less than the minimum width W (see FIG. 1) of the at least one lumen 12. Therefore, in the secure state of the insert 180, the at least one lumen 12 may not inadvertently dislocate from the first groove portion 186 and be received within the second groove portion 188.

As shown in FIG. 4, in some embodiments, in the release state, the two split insert portions 182 of the insert 180 may be moved away from each other relative to their respective positions in the secure state, such that the at least one lumen 12 is configured to be slidably received through the second groove portion 188 and insertable within the first groove portion 186.

In some embodiments, the main body 110 may define a maximum body height H1 in the closed configuration. In some embodiments, the insert 180 may define a maximum insert height H2 in the secure state, such that the maximum body height H1 is greater than the maximum insert height H2. Thus, the portion 174 of the main body may be defined between the first pivot interface 160 and the second pivot interface 162, such that a height H3 of the portion 174 may be substantially equal to a difference between the maximum body height H1 and the maximum insert height H2. Further, the height H3 may also be defined as a distance between the first pivot interface 160 and the second pivot interface 162, along the normal axis 172.

Figure 5:
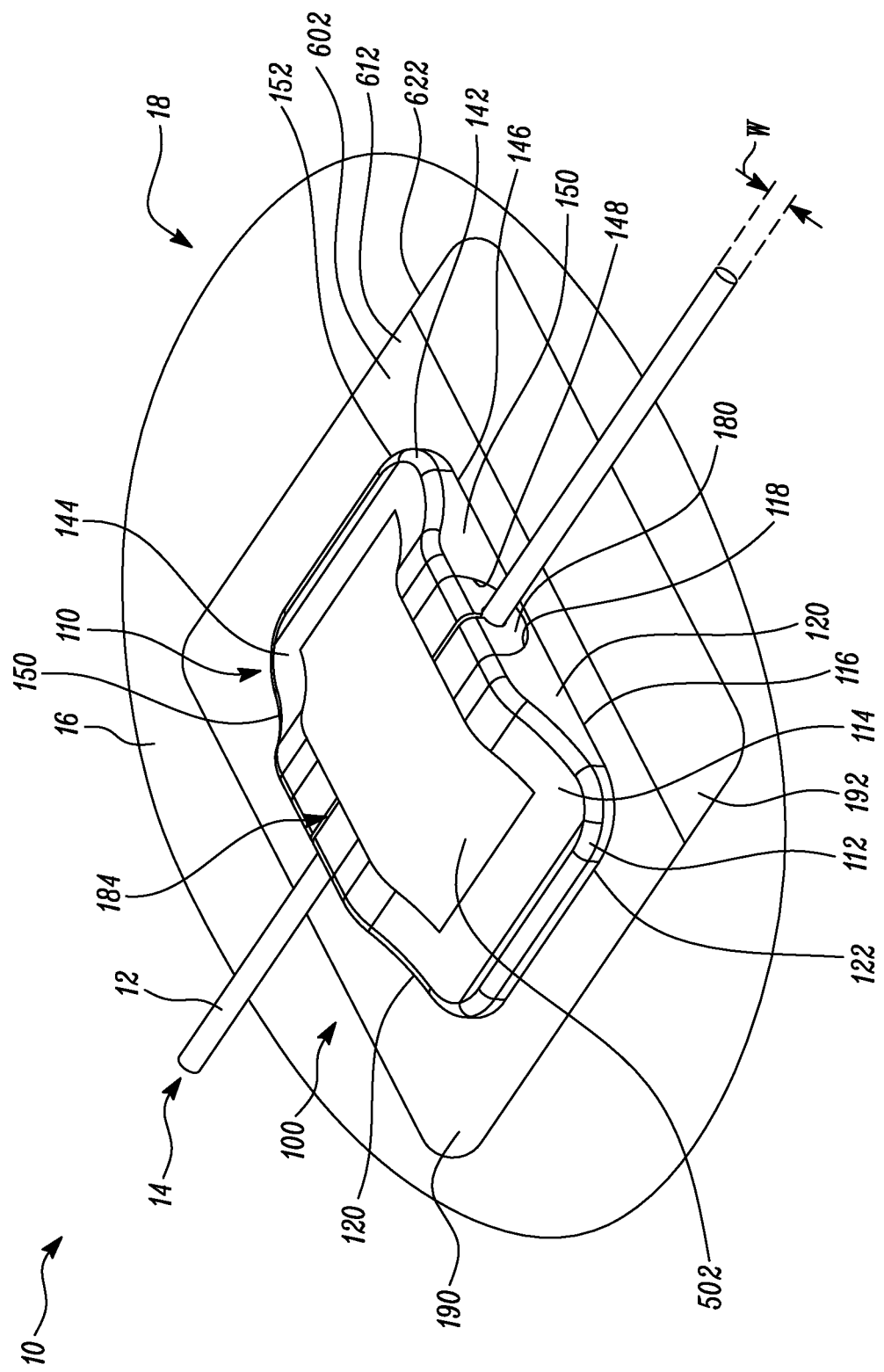
FIG. 5 is a schematic perspective view of the securement device secured to a skin of a user using a closure tape, according to an embodiment of the present disclosure.

Referring now to FIG. 5, in some embodiments, the securement device 100 may include a retaining means to maintain or retain the main body 110 in the closed configuration, after the insert 180 has at least partially and removably received the at least one lumen 12. In some embodiments, the securement device 100 further includes a closure tape 502. In some embodiments, the closure tape 502 may be adapted to be coupled to the first upper surface 114 of the first body portion 112 and the second upper surface 144 of the second body portion 142 for retaining the main body 110 in the closed configuration. In some embodiments, the closure tape 502 may be configured to be removably applied to the main body 110, such that the closure tape 502 may apply a downward force on the main body 110 in order to prevent the main body 110 from moving towards the open configuration. In some embodiments, the closure tape 502 may be secured to the first and second body portions 112, 142 of the main body 110. In other embodiments, the closure tape 502 may be secured to the main body 110 and the base 190 of the securement device 100. In yet other embodiments, the closure tape 502 may be further secured on the skin 16 (see FIG. 1) of the user 18 (see FIG. 1). In some embodiments, the closure tape 502 may be an adhesive tape suitable for medical applications.

The base 190 may include a first major surface 612 and a second major surface 614 (shown in FIG. 6) opposing the first major surface 612. In some embodiments, the first major surface 612 may be fixedly coupled to the first lower surface 116 of the first body portion 112 and the second lower surface 146 of the second body portion 142. In some embodiments, the second major surface 614 may be configured to at least partially engage and be detachably secured to the skin 16 of the user 18. In some embodiments, the base 190 may be a passive dressing. In other words, in some embodiments, the base 190 may be non-occlusive. However, in some embodiments, the base 190 may be an interactive dressing. In other words, in some embodiments, the base 190 may be semi-occlusive or occlusive. Therefore, in some embodiments, the base 190 may act as a barrier against penetration of bacteria. In some cases, the base 190 may maintain hydration of an area of the skin 16 at which the base 190 may be removably secured and may reduce infection of the area of the skin 16 at which the base 190 may be removably secured.

In some embodiments, the base 190 may be deformable based on the deformation of the main body 110 between the open configuration and the closed configuration. In some embodiments, the base 190 may have a curvilinear shape in the open configuration of the main body 110, as illustrated in FIG. 3. In some embodiments, the base 190 may have a substantially planar shape in the closed configuration of the main body 110, as illustrated in FIG. 4. In some embodiments, an area of the second major surface 614 of the base 190 may be greater than a sum of respective areas of the first lower surface 116 of the first body portion 112 and the second lower surface 146 of the second body portion 142. Therefore, the base 190 may have a larger area than an area of the main body 110 contacting the base 190.

Figure 6:
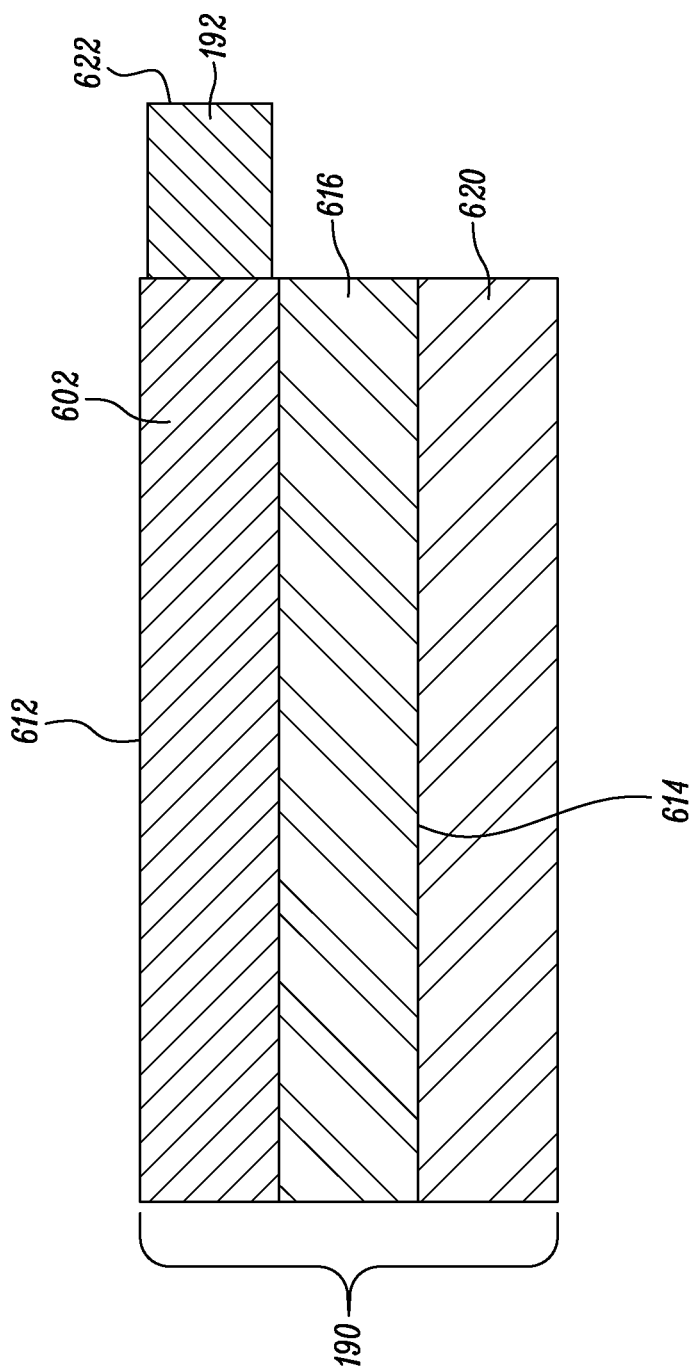
FIG. 6 is a schematic sectional view of the base of the securement device, according to an embodiment of the present disclosure.

Referring now to FIG. 6, in some embodiments, the base 190 may include a base body 602 including a stretchable polymeric material and forming the first major surface 612. The base 190 may be made of a stretchable material that may conform to undulated surfaces (e.g., the skin 16 of the user 18 illustrated in FIG. 1). Therefore, in some embodiments, the base 190 may be configured to exhibit high elasticity. In some embodiments, the base 190 may have a high tensile strength, a low elastic recovery, and a high elongation at break.

In some embodiments, the base body 602 of the base 190 may include at least one of a polymeric film, a polymeric foam, a polymeric hydrocolloid, and a polymeric alginate. In some embodiments, the base body 602 may include polyolefins, such as, polyethylene, including high density polyethylene, low density polyethylene, linear low density polyethylene, and linear ultra-low density polyethylene, polypropylene, and polybutylenes, vinyl copolymers, such as, polyvinyl chlorides, both plasticized and unplasticized, and polyvinyl acetates, olefinic copolymers, such as, ethylene/methacrylate copolymers, ethylene/vinyl acetate copolymers, acrylonitrile-butadiene-styrene copolymers, and ethylene propylene copolymers, acrylic polymers and copolymer, and combinations thereof. In some embodiments, the base body 602 may include a single layer film or multi-layer films, non-woven films, porous films, foam-like films, and combinations thereof. In some embodiments, the base body 602 may be fabricated using any suitable method of film forming, such as, extrusion, co-extrusion, solvent casting, foaming, non-woven technology, and the like.

In some embodiments, the base 190 may further include an adhesive layer 616 disposed on the base body 602 and at least partially forming the second major surface 614. In some embodiments, the adhesive layer 616 may include a stretch release adhesive.

In some cases, an adhesive strength of the stretch-release adhesive may be less than a cohesive strength of the stretch-release adhesive, such that upon stretching of the base 190, adhesion capabilities of the stretch-release adhesive may essentially disappear. Specifically, a tack of the stretch-release adhesive may be lost upon stretching of the base 190. Therefore, in some embodiments, the base 190 may be easily removed from the skin 16 of the user 18 based on the stretching of the base 190.

Further, the adhesive may be a pressure sensitive adhesive. In some embodiments, the adhesive may have a relatively high moisture vapor transmission rate to allow for moisture evaporation. In some embodiments, suitable pressure sensitive adhesives may include those based on acrylates, urethane, hydrogels, hydrocolloids, block copolymers, silicones, rubber-based adhesives (including natural rubber, polyisoprene, polyisobutylene, butyl rubber, etc.) as well as combinations of such adhesives. In some embodiments, an adhesive component of the pressure sensitive adhesive may contain tackifiers, plasticizers, rheology modifiers as well as active components, for example, an antimicrobial agent. In some embodiments, the pressure sensitive adhesive may be reasonably skin compatible and "hypoallergenic".

In some embodiments, the adhesive layer 616 may include a multi-layer elastomeric layer including elastomeric polymers, such as, styrene-ethylene-butylene-styrene (SEBS), styrene-ethylene-propylene-styrene (SEPS), styrene-isoprene-styrene (SIS), styrene-butadiene-styrene (SBS), polyurethane, ethyl vinyl acetate (EVA), ethyl methyl acrylate (EMA), ultra-low linear density polyethylene (ULLDPE), hydrogenated polypropylene, polypropylene, polyethylene, high density polyethylene (HDPE), low density polyethylene (LDPE), linear low density polyethylene (LLDPE), and combinations or blends thereof. Further, the adhesive layer 616 may be flood-coated or pattern-coated.

Figure 7:
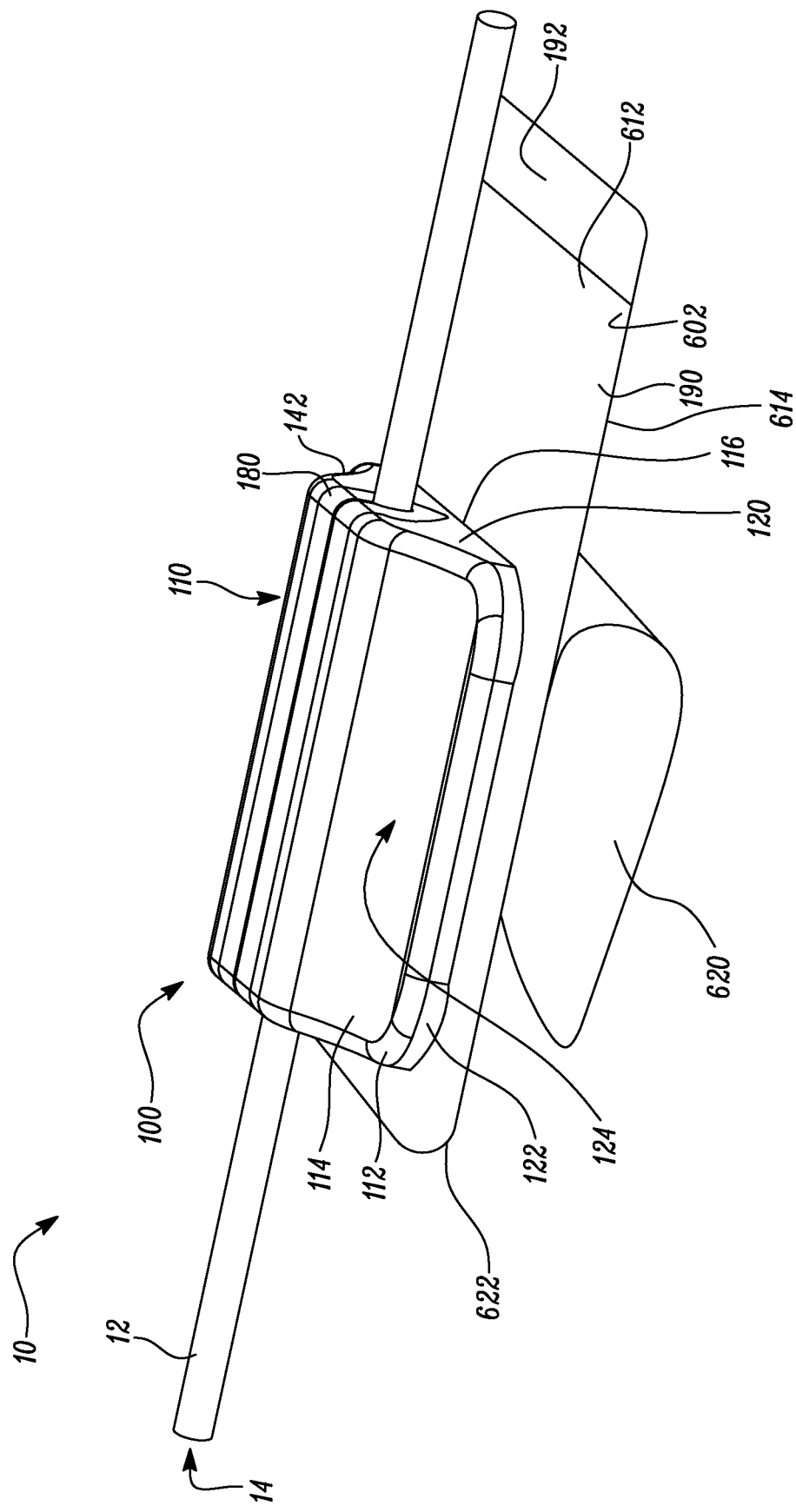
FIG. 7 is a schematic perspective view of the securement device illustrating removal of a release liner of the securement device, according to an embodiment of the present disclosure.

In some embodiments, the securement device 100 may further include a release liner 620 removably secured to the second major surface 614 of the base 190. In some embodiments, the release liner 620 may be removed from the base 190 for detachably securing the base 190 to the skin 16 of the user 18. FIG. 7 is a schematic perspective view of the securement device 100 illustrating a removal of the release liner 620, according to an embodiment of the present disclosure. In some embodiments, when the release liner 620 may be removed from the base 190, the adhesive layer 616 (see FIG. 6) of the base 190 may be exposed. Further, the exposed adhesive layer 616 may allow the base 190 to be detachably secured to the skin 16 of the user 18.

The release liner 620 may protect the adhesive layer 616 from contaminants, such as, dust, debris, and the like, prior to use of the securement device 100. The release liner 620 may be manufactured using a plastic base material. The release liner 620 may include a shape substantially similar to the shape of the base 190. The release liner 620 may be peeled off from the adhesive layer 616 prior to removable securement of the base 190 to the skin 16 of the user 18. The release liner 620 may include any suitable material, such as, Polyethylene Terephthalate (PET), High-Density Polyethylene (HDPE), Polyvinyl Chloride (PVC), Polypropylene (PP), and the like.

In some embodiments, the base 190 may further include one or more pull tabs 192 disposed at the perimeter 622 of the base 190 and free of the adhesive layer 616. In the illustrated embodiment of FIG. 7, the base 190 includes the single pull tab 192. Alternatively, the base 190 may include two pull tabs disposed at opposing ends of the base 190. The pull tab 192 may be embodied as adhesive free zones, such that the pull tab 192 may not attach to the skin 16 of the user 18. The pull tab 192 may be configured to be gripped to detach the base 190 from the skin 16. Specifically, the pull tab 192 may allow gripping of the base 190 for application and removal of the securement device 100 and may also allow the clinician or any other medical professional to peel-off the release liner 620 for application of the securement device 100 onto the skin 16 of the user 18. Further, in some embodiments, for removal of the base 190 from the skin 16 of the user 18, the base 190 may be stretched by gripping and pulling the pull tab 192.

Figure 8:
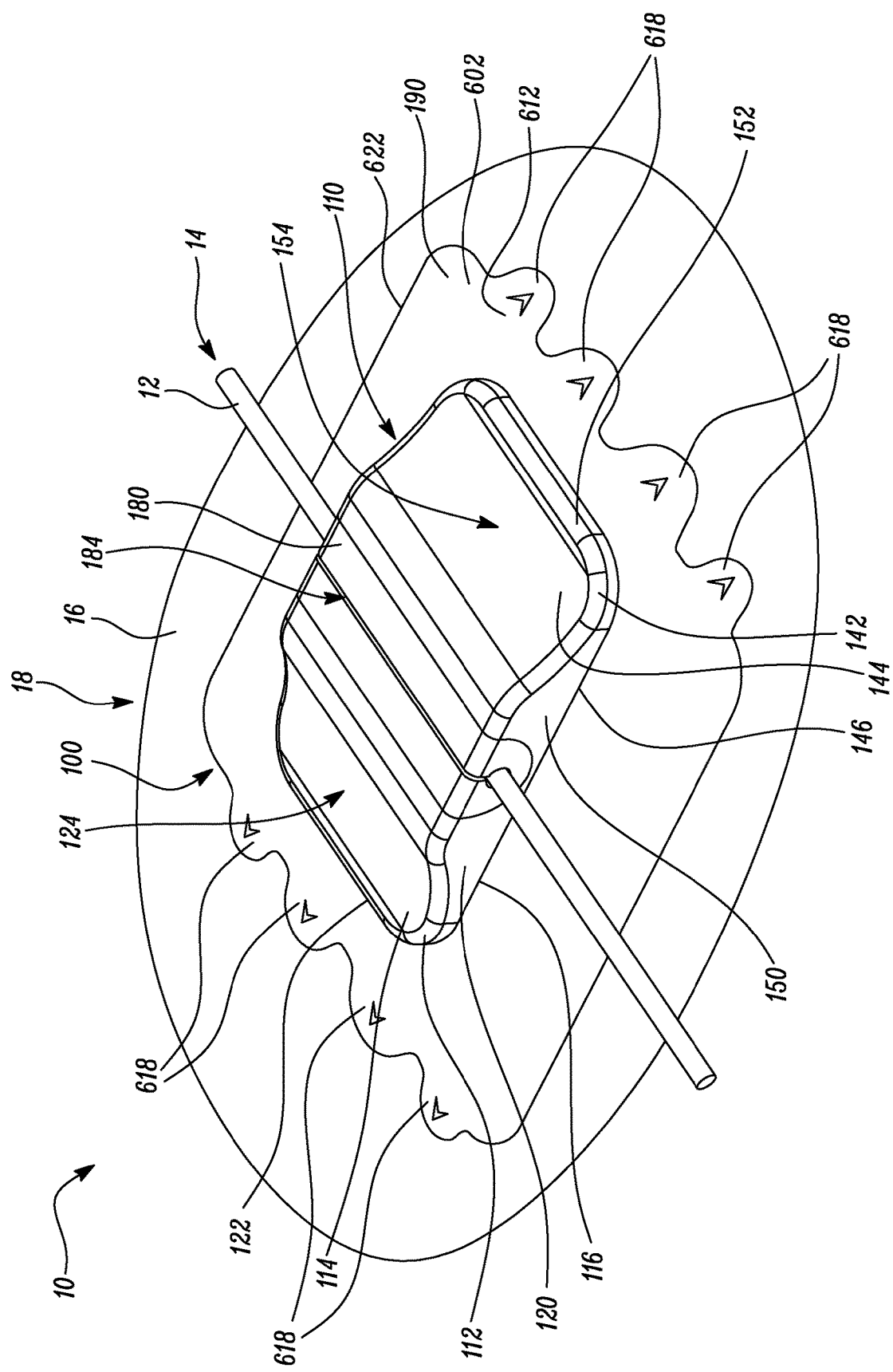
FIG. 8 is a schematic perspective view of the securement device, wherein the base of the securement device includes a number of pull tabs, according to an embodiment of the present disclosure.

Referring now to FIG. 8, the base 190 may include a plurality of pull tabs 618 instead of the single pull tab 192 (see FIG. 7). Specifically, in the illustrated embodiment of FIG. 8, the base 190 includes four pairs of pull tabs 618, i.e., eight pull tabs 618 in total. The pull tabs 618 may be substantially semi-circular in shape. In other embodiments, the pull tabs 618 may include any other shape or number of the pull tabs 618, without any limitations. In some examples, the pull tabs 618 may include markings thereon that indicate a direction along which the pull tabs 618 may have to be pulled for removal of the securement device 100. The pull tabs 618 may be embodied as adhesive free zones, such that the pull tabs 618 may not attach to the skin 16 (see FIG. 1) of the user 18 (see FIG. 1). The pull tabs 618 may be configured to be gripped to detach the base 190 from the skin 16. Specifically, the pull tabs 618 may allow gripping of the base 190 for application and removal of the securement device 100 and may also allow the clinician or any other medical professional to peel-off the release liner 620 for application of the securement device 100 onto the skin 16 of the user 18. Further, in some embodiments, for removal of the base 190 from the skin 16 of the user 18, the base 190 may be stretched by gripping and pulling the pull tabs 618.

Figure 9:
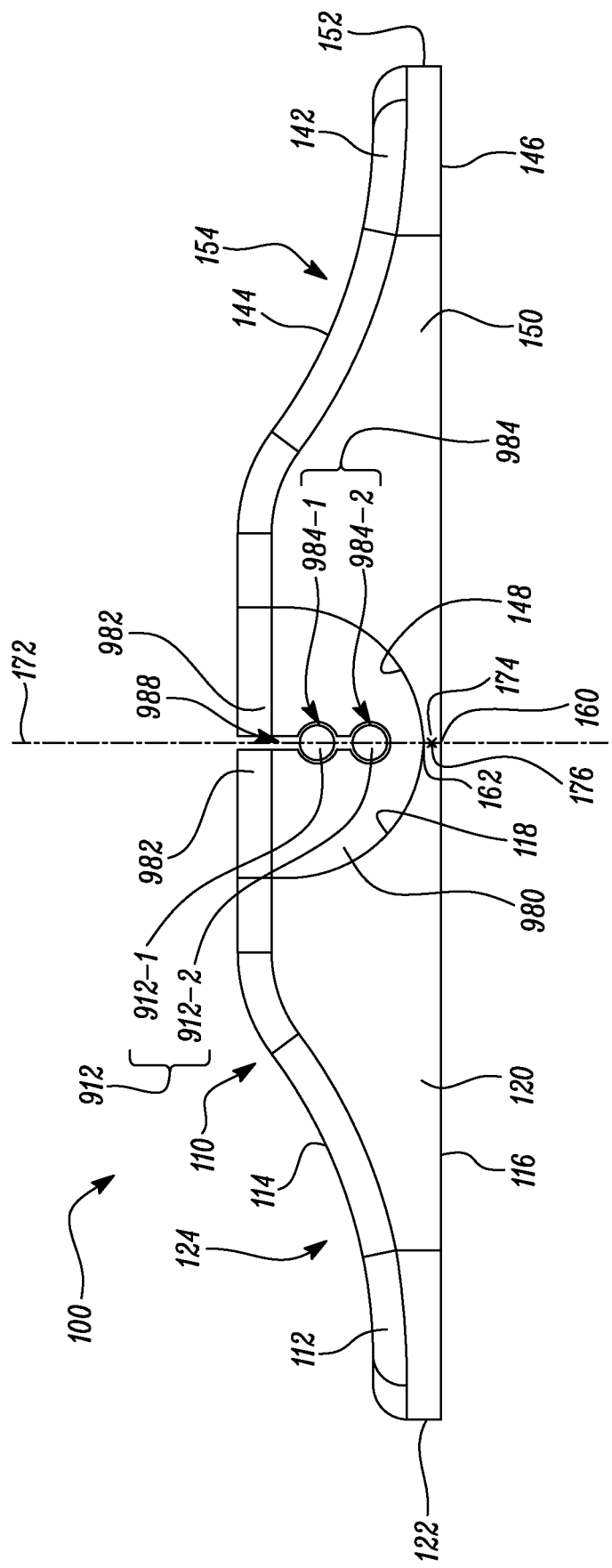
FIG. 9 is a schematic side view of the securement device with the base not shown, according to another embodiment of the present disclosure.

FIG. 9 illustrates a schematic side view of the securement device 100, according to another embodiment of the present disclosure. The base 190 is not shown in FIG. 9 for the purpose of clarity. In some embodiments, the securement device 100 includes an insert 980. The insert 980 may be substantially similar to the insert 180 (see FIG. 2B). However, the insert 980 may be configured to receive a plurality of lumens 912. In some embodiments, the insert 980 may include a plurality of grooves 984, such that each groove 984-1, 984-2 at least partially and slidably receives a corresponding lumen 912-1, 912-2 from the plurality of lumens 912. In the illustrated embodiment of FIG. 9, the insert 980 includes two grooves 984-1, 984-2. The grooves 984-1, 984-2 are configured to at least partially and slidably receive the lumens 912-1, 912-2, respectively. The grooves 984-1, 984-2 may have a generally circular shape when the insert is in the secure state. In some examples, the insert 980 may include more than two grooves, as per application requirements. The insert 980 further includes a groove portion 988, similar to the groove portion 188 (see FIG. 4), and two split insert portions 982 defining the groove portion 988 therebetween, such that the groove portion 988 is open. The groove portion 988 may have a generally rectangular shape when the insert is in the secure state.

With reference to FIG. 1, therefore, the securement device 100 may secure the medical device 14 firmly onto the skin 16 of the user 18. Furthermore, the securement device 100 may inhibit movement of the medical device 14. Consequently, the securement device 100 may prevent various complications that may occur due to micro-movement of the medical device 14.

Figure 10:
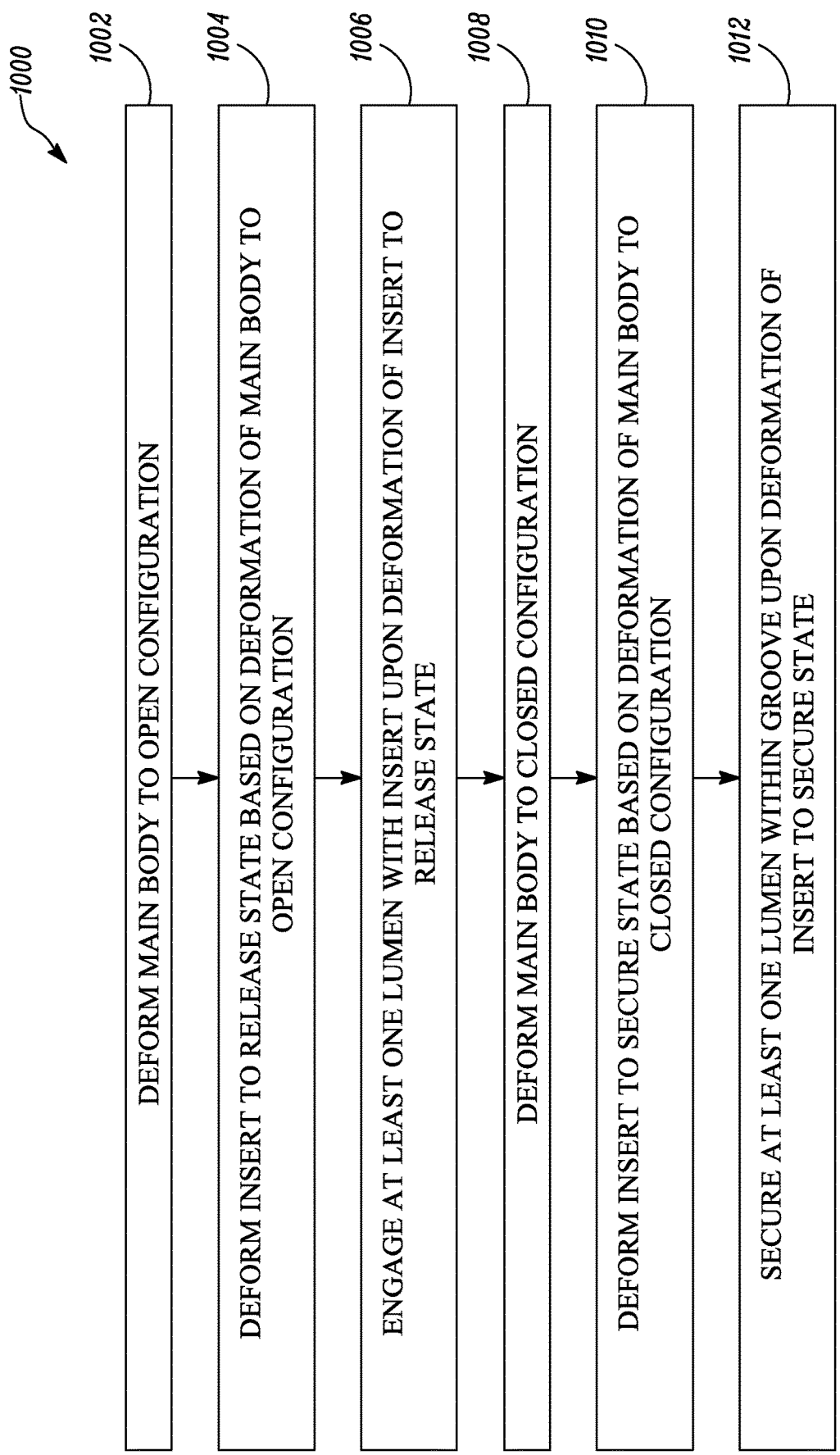
FIG. 10 illustrates a flowchart depicting a method of securing the securement device on the skin of the user, according to an embodiment of the present disclosure.

FIG. 10 illustrates a flowchart depicting a method 1000 of securing the securement device 100 on the skin 16 of the user 18, according to an embodiment of the present disclosure. FIGS. 11A to 11F illustrate various steps of securing the securement device 100 to the skin 16 of the user 18, according to an embodiment of the present disclosure. The method 1000 will hereinafter be described with reference to FIGS. 10, and FIGS. 11A-11F. The securement device 100 includes the main body 110 including the first body portion 112 and the second body portion 142, and the insert 180 fixedly coupled to the main body 110. Referring to FIGS. 10, 11A, and 11B, at step 1002, the main body 110 is deformed to the open configuration. Specifically, the main body 110 is deformed from the closed configuration as shown in FIG. 11A to the open configuration as shown in FIG. 11B. In the open configuration of the main body 110, the first lower surface 116 of the first body portion 112 and the second lower surface 146 of the second body portion 142 are inclined to each other at the first pivot interface 160. At step 1004, the insert 180 is deformed to the release state based on the deformation of the main body 110 to the open configuration. The release state of the insert 180 corresponds to the open configuration of the main body 110. In some embodiments, the main body 110 and the insert 180 are deformed about the common pivot axis 176.

Referring to FIGS. 10 and 11C, at step 1006, the at least one lumen 12 engages with the insert 180 upon the deformation of the insert 180 to the release state. When the insert 180 is in the release state, the groove 184 of the insert 180 is configured to removably and at least partially receive the at least one lumen 12 therein.

Referring to FIGS. 10 and 11D, at step 1008, the main body 110 is deformed to the closed configuration. In the closed configuration of the main body 110, the first lower surface 116 of the first body portion 112 and the second lower surface 146 of the second body portion 142 are substantially parallel to each other at the first pivot interface 160. At step 1010, the insert 180 is deformed to the secure state based on the deformation of the main body 110 to the closed configuration. The secure state of the insert 180 corresponds to the closed configuration of the main body 110. At step 1012, the at least one lumen 12 is secured within the groove 184 upon the deformation of the insert 180 to the secure state.

Referring to FIGS. 10, 11E, and 11F, in some embodiments, the base 190 may engage with the skin 16 of the user 18. As shown in FIG. 11E, in some embodiments, the release liner 620 may be removably secured to the second major surface 614 of the base 190. In some embodiments, the release liner 620 may be removed from the base 190 prior to detachably securing the base 190 to the skin 16 of the user 18.

The base 190 may include the first major surface 612 and the second major surface 614 opposing the first major surface 612. The first major surface 612 may be fixedly coupled to the first lower surface 116 of the first body portion 112 and the second lower surface 146 of the second body portion 142. Further, the second major surface 614 may be configured to at least partially engage and be detachably secured to the skin 16 of the user 18. Moreover, the base 190 may be deformable based on the deformation of the main body 110 between the open configuration and the closed configuration. As illustrated in FIGS. 11B and 11C, the base 190 may have a curvilinear shape in the open configuration of the main body 110. Further, as illustrated in FIG. 11D, the base 190 may have a substantially planar shape in the closed configuration of the main body 110.

Referring to FIGS. 5 and 10, in some embodiments, the method 1000 may include a step of coupling the closure tape 502 to the first upper surface 114 of the first body portion 112 and the second upper surface 144 of the second body portion 142 for retaining the main body 110 in the closed configuration. Furthermore, in some embodiments, the one or more pull tabs 192, 618 (see FIGS. 7 and 8, respectively) may be gripped to detach the base 190 from the skin 16.

Moreover, in some embodiments, the insert 980 (see FIG. 9) may include the plurality of grooves 984 (see FIG. 9), such that each groove 984-1, 984-2 (see FIG. 9) may at least partially and slidably receive the corresponding lumen 912-1, 912-2 (see FIG. 9) from the plurality of lumens 912 (see FIG. 9). Accordingly, the plurality of lumens 912 may be at least partially received within the insert 980.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A securement device for securing at least one lumen of a medical device, the securement device comprising:
    a main body having a first modulus of elasticity and configured to be detachably secured to a skin of a user, the main body comprising:
        a first body portion comprising a first upper surface, a first lower surface opposing the first upper surface, and a first cavity surface extending from the first upper surface partially towards the first lower surface; and a second body portion pivotally coupled to the first body portion, the second body portion comprising a second upper surface spaced apart from the first upper surface, a second lower surface pivotally coupled to the first lower surface along a first pivot interface, and a second cavity surface extending from the second upper surface partially towards the second lower surface, wherein the second cavity surface is pivotally coupled to the first cavity surface along a second pivot interface spaced apart from the first pivot interface, and wherein the first cavity surface and the second cavity surface together define a cavity of the main body disposed between the first upper surface and the second upper surface; and an insert fixedly coupled to the main body and at least partially received within the cavity of the main body, the insert engaging at least the first cavity surface of the first body portion, the second cavity surface of the second body portion, and the second pivot interface, the insert comprising a groove along its length and having a second modulus of elasticity less than the first modulus of elasticity, wherein the insert is configured to at least partially and removably receive the at least one lumen within the groove; and wherein the main body is deformable between an open configuration and a closed configuration, wherein the insert is deformable between a release state and a secure state based on a deformation of the main body between the open configuration and the closed configuration, wherein the release state of the insert corresponds to the open configuration of the main body and the secure state of the insert corresponds to the closed configuration of the main body;

wherein, in the open configuration of the main body:
the first lower surface of the first body portion and the second lower surface of the second body portion are inclined to each other at the first pivot interface; and
the insert is in the release state, such that the groove is configured to removably and at least partially receive the at least one lumen therein; and wherein, in the closed configuration of the main body:
the first lower surface of the first body portion and the second lower surface of the second body portion are substantially parallel to each other at the first pivot interface; and
the insert is in the secure state, such that the at least one lumen is secured within the groove.

2. The securement device of claim 1, further comprising a base comprising a first major surface and a second major surface opposing the first major surface, wherein the first major surface is fixedly coupled to the first lower surface of the first body portion and the second lower surface of the second body portion, wherein the second major surface is configured to at least partially engage and be detachably secured to the skin of the user, wherein the base is deformable based on the deformation of the main body between the open configuration and the closed configuration, wherein the base has a curvilinear shape in the open configuration of the main body, and wherein the base has a substantially planar shape in the closed configuration of the main body.

3. The securement device of claim 2, wherein the base comprises:
a base body comprising a stretchable polymeric material and forming the first major surface; and an adhesive layer disposed on the base body opposite to the main body and at least partially forming the second major surface, the adhesive layer comprising a stretch release adhesive.

4. The securement device of claim 3, wherein the base further comprises one or more pull tabs disposed at a perimeter of the base and free of the adhesive layer, and wherein the one or more pull tabs are configured to be gripped to detach the base from the skin.

5. The securement device of claim 2, wherein an area of the second major surface of the base is greater than a sum of respective areas of the first lower surface of the first body portion and the second lower surface of the second body portion.

6. The securement device of claim 2, further comprising a release liner removably secured to the second major surface of the base, wherein the release liner is removed from the base for detachably securing the base to the skin of the user.

7. The securement device of claim 1, wherein the main body is a single-piece integral component.

8. The securement device of claim 1, wherein the main body comprises at least one of a polymer, an elastomer, and a metal.

9. The securement device of claim 1, wherein the insert comprises an elastomer.

10. The securement device of claim 1, wherein the first elastic modulus of the main body is greater than the second elastic modulus of the insert by a factor of at least 2.

11. The securement device of claim 1, wherein the first body portion further comprises:
a pair of first lateral surfaces opposing each other and extending between the first upper surface and the first lower surface; and
a first end surface disposed distal to the first cavity surface and extending between the pair of first lateral surfaces, wherein the first end surface is further disposed between the first upper surface and the first lower surface.

12. The securement device of claim 11, wherein the first cavity surface extends between the pair of first lateral surfaces.

13. The securement device of claim 11, wherein the insert extends between the pair of first lateral surfaces.

14. The securement device of claim 11, wherein the first body portion tapers at least partially from the cavity towards the first end surface, such that the first body portion further comprises a first gripping region disposed adjacent to the first end surface.

15. The securement device of claim 11, wherein the second body portion further comprises:
a pair of second lateral surfaces opposing each other and extending between the second upper surface and the second lower surface; and
a second end surface disposed distal to the second cavity surface and extending between the pair of second lateral surfaces, wherein the second end surface is further disposed between the second upper surface and the second lower surface; and
wherein each of the pair of second lateral surfaces is joined to a corresponding first lateral surface from the pair of first lateral surfaces of the first body portion between the first pivot interface and the second pivot interface.

16. The securement device of claim 15, wherein the second cavity surface extends between the pair of second lateral surfaces.

17. The securement device of claim 15, wherein the insert extends between the pair of second lateral surfaces.

18. The securement device of claim 15, wherein the second body portion tapers at least partially from the cavity towards the second end surface, such that the second body portion further comprises a second gripping region disposed adjacent to the second end surface.

19. The securement device of claim 1, wherein the first upper surface is curved, and the first lower surface is substantially planar.

20. The securement device of claim 1, wherein the second upper surface is curved, and the second lower surface is substantially planar.

21. The securement device of claim 1, further comprising a closure tape adapted to be coupled to the first upper surface of the first body portion and the second upper surface of the second body portion for retaining the main body in the closed configuration.

22. The securement device of claim 1, wherein the cavity has a first maximum cavity width in the open configuration of the main body and a second maximum cavity width in the closed configuration of the main body, and wherein the first maximum cavity width is greater than the second maximum cavity width.

23. The securement device of claim 1, wherein the groove of the insert comprises a first groove portion disposed proximal to the second pivot interface and a second groove portion extending from the first groove portion away from the second pivot interface, wherein the insert comprises two split insert portions defining the second groove portion therebetween, such that the second groove portion is open, wherein, in the secure state, a first maximum groove width of the first groove portion is greater than a second maximum groove width of the second groove portion by a factor of at least 2 and the at least one lumen is secured within the first groove portion, and wherein, in the release state, the two split insert portions of the insert are moved away from each other relative to their respective positions in the secure state, such that the at least one lumen is configured to be slidably received through the second groove portion and insertable within the first groove portion.

24. The securement device of claim 23, wherein, in the secure state of the insert, the first groove portion comprises a circular cross-sectional shape and the second groove portion comprises a rectangular cross-sectional shape.

25. The securement device of claim 23, wherein, in the secure state of the insert, the second maximum groove width of the second groove portion is less than a minimum width of the at least one lumen.

26. The securement device of claim 1, wherein the main body and the insert are deformable about a common pivot axis.

27. The securement device of claim 1, wherein the insert is configured to receive a plurality of lumens.

28. The securement device of claim 27, wherein the insert comprises a plurality of grooves, such that each groove at least partially and slidably receives a corresponding lumen from the plurality of lumens.

29. The securement device of claim 1, wherein the main body defines a maximum body height in the closed configuration and the insert defines a maximum insert height in the secure state, such that the maximum body height is greater than the maximum insert height.

* * * * *